US00PP07954P

United States Patent [19]

van der Knaap

[11] Patent Number: Plant 7,954

[45] Date of Patent: Aug. 25, 1992

[54] CHRYSANTHEMUM PLANT—YELLOW DAYMARK CULTIVAR

[75] Inventor: Jacques C. M. van der Knaap, De Lier, Netherlands

[73] Assignee: Fides Beheer B.V., De Lier, Netherlands

[21] Appl. No.: 577,696

[22] Filed: Sep. 5, 1990

[51] Int. Cl.[5] ..... A01H 5/00

[52] U.S. Cl. ..... Plt./82.2

[58] Field of Search ..... Plt./74, 82.1, 82.2

[56] References Cited

U.S. PATENT DOCUMENTS

P.P. 6,240 8/1988 van der Knaap ..... Plt. 74
4,616,099 10/1986 Sparkes ..... 47/58

OTHER PUBLICATIONS

Chan 1966, "Chrysanthemum and Rose Mutations Induced by X-Rays", Proc. Am. Soc. Hort. Sci., vol. 88: 613-620.

Broertjes, 1966, "Mutation Breeding of Chrysanthemums", Euphytica 15:156-162.

Dowrick et al., 1966, The Induction of Mutations in Chrysanthemum Using X-and Gamma Radiation, Euphytica 15:204-210.

Broertjes et al., 1980, "A Mutant of a Mutant of a Mutant of a . . . Irradiation of Progressive Radiation-Induced Mutants in a Mutation Breeding Programme with *C. Morifolium* Ram", Euphytica 29:525-530.

Gosling, ed. 1979, *The Chrysanthemum Manual of the National Chrysanthemum Society,* Essex Telegraph Press, Ltd., Colchester, England, pp. 329-336.

Broertjes et al., 1978, "Application of Mutation Breeding Methods in the Improvement of Vegetatively Propagated Crops", Elsevier Scientific Pub. Co., New York, pp. 162-175.

Searle et al., 1968, *Chrysanthemums the Year Round,* Blandford Press, London England, pp. 27-29, 320-327.

*Primary Examiner*—Howard J. Locker

*Attorney, Agent, or Firm*—Burns, Doane, Swecker & Mathis

[57] ABSTRACT

A new and distinct cultivar of Chrysanthemum plant named Yellow Daymark is provided. The new cultivar was the result of a mutation induced by controlled irradiation with x-rays and can be readily distinguished from the parent Daymark cultivar (U.S. Plant Pat. No. 6,240). More specifically, the new cultivar exhibits attractive bright yellow ray and disc florets which can be readily distinguished from the white blossom coloration of the parent cultivar. A larger number of petals are present than on the parent cultivar. Also, the new cultivar has been found to exhibit a more compact growth habit with less vegetative growth and to exhibit a lesser plant height than the parent cultivar under the same growing conditions. The new cultivar is particularly suited for use in the production of a cut anemone spray.

1 Drawing Sheet

SUMMARY OF THE INVENTION

The present invention comprises a new and distinct cultivar of *Dendranthema morifolium* Ramat., and hereinafter is referred to by the cultivar name Yellow Daymark.

The new cultivar is a mutation which was induced in a plant of the Daymark cultivar (U.S. Plant Pat. No. 6,240) by irradiation with x-rays at a level of 1750 rads. The discovery of the new cultivar was made at De Lier, The Netherlands, during October, 1985. This discovery resulted in the identification of a single plant of the new cultivar.

It has been found that the new cultivar of the present invention:

(a) exhibits attractive bright yellow ray and disc florets which can be distinguished from the white blossom coloration of the Daymark cultivar (U.S. Plant Pat. No. 6,240), (b) exhibits a more compact growth habit with less vegetative growth and assumes a lesser plant height than the Daymark cultivar under the same growing conditions, and (c) forms blossoms having a larger number petals than the Daymark cultivar.

This combination of characteristics is capable of well distinguishing the new Yellow Daymark cultivar from the Daymark cultivar and from all other known Chrysanthemum cultivars. The new cultivar is particularly suited for use in the production of a cut anemone spray.

Asexual reproduction of the new cultivar by cuttings, as performed at De Lier, The Netherlands, has demonstrated that the characteristics of the new cultivar as herein disclosed are firmly fixed and are retained through successive generations of asexual propagation.

Yellow Daymark has not been observed under all possible environmental conditions to date. Accordingly, it is possible that the phenotype may vary somewhat with variations in the environment, such as temperature, light, day length, contact with pesticides and/or subjection to growth retardant treatments.

In my companion application Ser. No. 07/577,750, filed concurrently herewith, entitled "Chrysanthemum Plant — Cream Daymark Cultivar" is claimed a related cultivar in which the ray and disc florets exhibit a distinctive light yellow or cream coloration.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands.

Classification:

*Botanical.*—*Dendranthema morifolium* Ramat., cv. Yellow Daymark.

*Commercial.*—Cut anemone spray.

Inflorescence

A. Capitulum:

*Form.*—Flat.

*Type.*—Anemone.

*Diameter across face.*—Approximately 70 mm. on average.

*Diameter across disc.*—Approximately 26 mm. on average.

B. Corolla of ray and disc florets:

*Color (general tonality from a distance of one meter)*.—Bright yellow.

*Color ray (top surface)*.—Approximates Yellow Group 3B.

*Color ray (under surface)*.—Approximates Yellow Group 6C.

*Color (disc)*.—Yellow-Green Group 154C changing to Yellow Group 6C.

*Number of ray florets.*—Approximately 34 on average.

*Number of disc florets.*—Approximately 140 to 150 on average.

C. Reproductive organs:

*Androecium.*—Present in disc florets; numerous.

*Gynoecium.*—Present in both disc and ray florets; numerous.

Plant

A. General appearance:

*Height.*—Approximately 80 to 85 cm. on average.

B. Foliage:

*Color (upper surface)*.—Yellow-Green Group 147A.

*Leaf size.*—Approximately 120×80 mm. on average.

*Branching laterals.*—Approximately 16 on average.

C. Response time: The response time is approximately 8 weeks.

The plants of the new Yellow Daymark cultivar can be distinguished from the parent Daymark cultivar (U.S. Plant Pat. No. 6,240) as well as its sister Cream Daymark cultivar (Ser. No. 577,750, filed Sep. 5, 1990), both with respect to blossom coloration and other characteristics. The following data was obtained during Nov. 1991 by a comparison of plants of the Daymark, Yellow Daymark and Cream Daymark cultivars growing in a nursery at De Lier, The Netherlands.

| | DAYMARK Cultivar | YELLOW DAYMARK Cultivar | CREAM DAYMARK Cultivar |
|---|---|---|---|
| Ray Floret Coloration | White Group 155D | Yellow Group 3B | Yellow Group 5D |
| Disk Floret Coloration | Yellow-Green Group 145D changing to White Group 155A | Yellow-Green Group 154C changing to Yellow Group 6C | Yellow-Green Group 145A changing to Yellow Group 4C |
| Plant Height at Harvest Stage | 85-90 cm. | 80-85 cm. | 80 cm. |
| Number of Ray Florets (on average) | 25 | 34 | 30 |
| Number of Disc Florets (on average) | 110-120 | 140-150 | 130-140 |
| Flower Diameter | 75 mm. | 70 mm. | 70 mm. |
| Disc Diameter | 22 mm. | 26 mm. | 26 mm. |
| Number of Laterals (average) | 18 | 16 | 20 |
| Typical Leaf Size | 110 × 80 mm. | 120 × 80 mm. | 120 × 90 mm. |
| Foliage Coloration | Yellow-Green Group 147A | Yellow-Green Group 147A | Yellow-Green Group 147A |
| Response Time | 7½ weeks | 8 weeks | 8 weeks |

No clear distinctions with respect to petal shape and disease resistance have been observed to date with respect to the Daymark, Yellow Daymark and Cream Daymark cultivars.

I claim:

1. A new and distinct cultivar of Chrysanthemum plant named Yellow Daymark, substantially as herein shown and described, which:

(a) exhibits attractive bright yellow ray and disc florets which can be distinguished from the white blossom coloration of the Daymark cultivar (U.S. Plant Pat. No. 6,240), (b) exhibits a more compact growth habit with less vegetative growth and assumes a lesser plant height than the Daymark cultivar under the same growing conditions, and (c) forms blossoms having a larger number of petals than the Daymark cultivar.

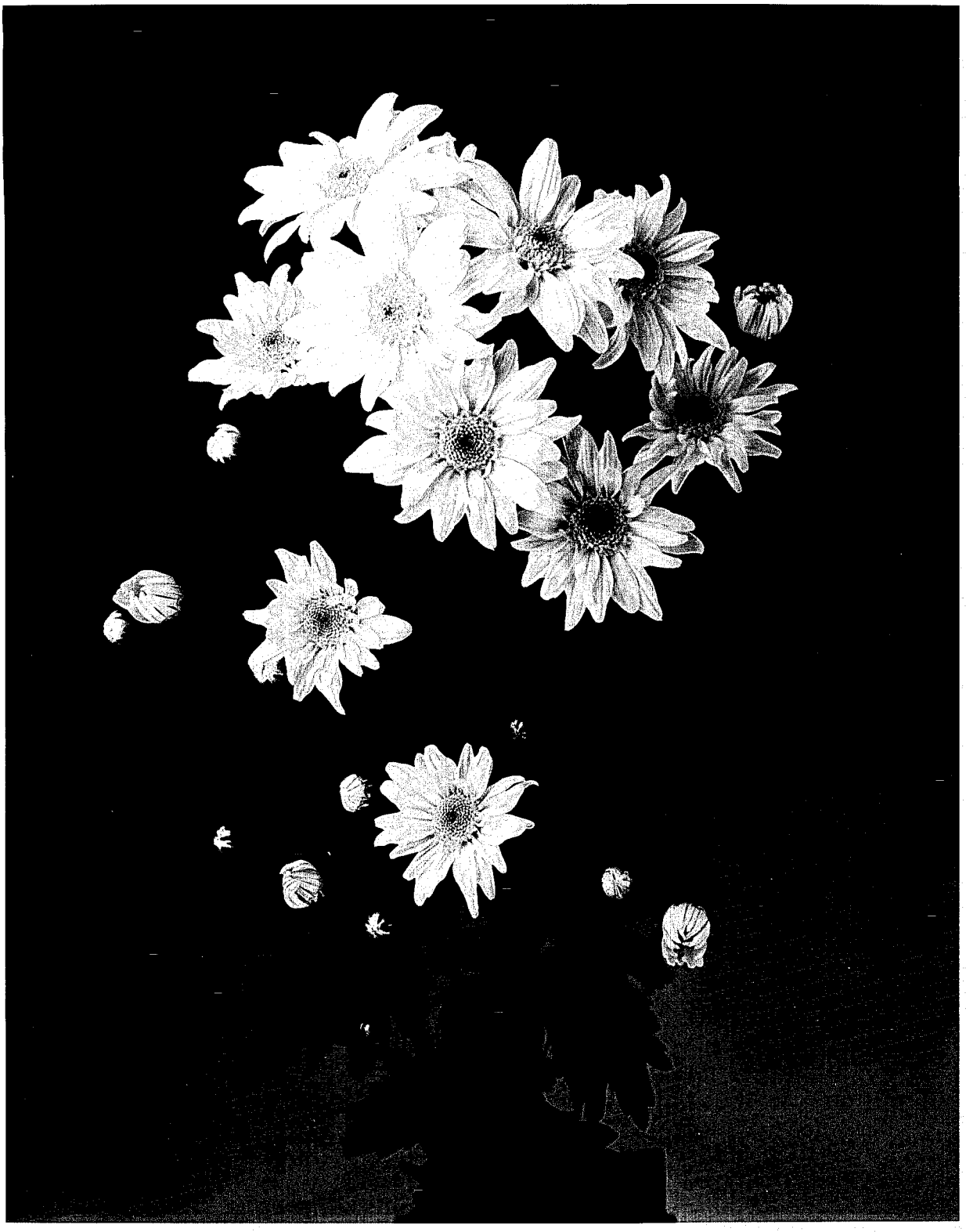

* * * * *